United States Patent [19]

Moran et al.

[11] 4,260,756

[45] Apr. 7, 1981

[54] 6- AND 8-HETEROARYL-1,2,4-TRIAZOLO[4,3-B]PYRIDAZINES

[75] Inventors: Daniel B. Moran, Suffern; John P. Dusza; Jay D. Albright, both of Nanuet, all of N.Y.

[73] Assignee: American Cyanamid Company, Stamford, Conn.

[21] Appl. No.: 94,628

[22] Filed: Nov. 15, 1979

[51] Int. Cl.[3] .................. C07D 237/00; A61K 31/495
[52] U.S. Cl. ................................. 544/236; 424/250
[58] Field of Search .......................................... 544/236

[56] References Cited

U.S. PATENT DOCUMENTS 3,915,968 10/1975 Bellasio et al. .................. 544/236

FOREIGN PATENT DOCUMENTS 1527537 5/1968 France ............................. 544/236

OTHER PUBLICATIONS

I. Lundina et al., Chem. Abstracts 67:21884q (1967) Some Tetrazdo (1,5-b)-and S-Triazolo (4,3-b) pyridazines and Their IR Characteristics.

*Primary Examiner*—Donald G. Daus
*Assistant Examiner*—M. C. Eakin

[57] ABSTRACT

This disclosure describes novel 6- and 8-heteroaryl and substituted 6- and 8-heteroaryl-1,2,4-triazolo[4,3-b]-pyridazines and their use as agents for treating anxiety.

14 Claims, No Drawings

6- AND 8-HETEROARYL-1,2,4-TRIAZOLO[4,3-B]PYRIDAZINES

BRIEF SUMMARY OF THE INVENTION

This invention relates to new organic compounds and more particularly is concerned with novel 6- and 8-heteroaryl and substituted 6- and 8-heteroaryl-1,2,4-triazolo-[4,3-b]pyridazines which may be represented by the following structural formula:

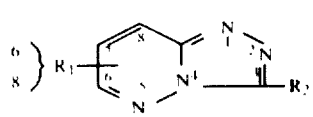

wherein $R_1$ is selected from the group consisting of:

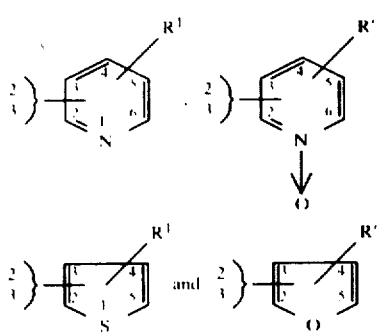

where R' is hydrogen and lower alkyl ($C_1$-$C_3$); and $R_2$ is hydrogen and lower alkyl ($C_1$-$C_3$).

The invention also includes novel compositions of matter containing the above-defined compounds useful as anxiolytic agents and the method of meliorating anxiety in mammals therewith.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, dimethylformamide, acetone, chloroform, ethyl acetate, and the like. They are appreciably soluble in non-polar organic solvents such as toluene, carbon tetrachloride, and the like but are relatively insoluble in water. The organic bases of this invention form non-toxic acid-addition salts with a variety of pharmacologically acceptable organic and inorganic salt-forming reagents. Thus, acid-addition salts, formed by admixture of the organic free base with one or two equivalents of an acid, suitably in a neutral solvent, are formed with such acids as sulfuric, phosphoric, hydrochloric, hydrobromic, sulfamic, citric, lactic, malic, succinic, tartaric, gluconic, ascorbic, and the like. The acid-addition salts are relatively insoluble in non-polar organic solvents such as diethyl ether, benzene, toluene, and the like. For purposes of this invention, the free bases are equivalent to their non-toxic acid-addition salts.

The novel 6-heteroaryl substituted compounds of the present invention may be readily prepared in accordance with the following reaction scheme:

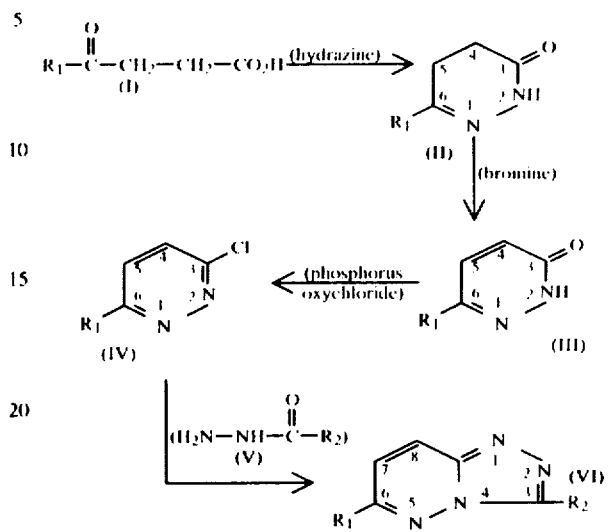

wherein $R_1$ and $R_2$ are as hereinabove described. In accordance with the above reaction scheme, an appropriately substituted 3-(heteroaroyl)propionic acid (I) is reacted with hydrazine hydrate at the reflux temperature in a lower alkanol solvent for a period of 12–24 hours to provide the corresponding 4,5-dihydro-6-heteroaryl-3(2H)-pyridazinone (II). Treatment of the 4,5-dihydro-6-heteroaryl-3(2H)-pyridazinone (II) with bromine in glacial acetic acid solvent at steam bath temperature for a period of 2–4 hours provides the corresponding 6-heteroaryl-3(2H)-pyridazinone (III). Conversion of the 6-heteroaryl-3(2H)-pyridazinone (III) to the corresponding 3-chloro-6-heteroarylpyridazine (IV) is achieved by treatment with excess phosphorus oxychloride at steam bath temperature for a period of 4–8 hours. Interaction of the 3-chloro-6-heteroarylpyridazine (IV) with an acylhydrazine (V) at the reflux temperature in a lower alkanol solvent for a period of 24–48 hours provides the corresponding 6-heteroaryl-1,2,4-triazolo[4,3-b]pyridazines (VI) of the present invention.

The novel 6-heteroaryl-1,2,4-triazolo[4,3-b]pyridazines of the present invention may also be prepared in accordance with the following reaction scheme:

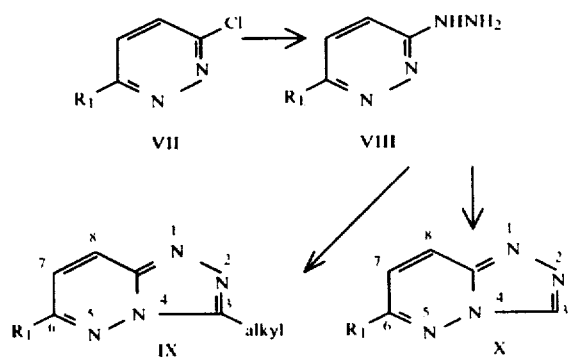

wherein $R_1$ is as hereinabove defined. In accordance with the above reaction scheme, 6-heteroaryl-3- chloropyridazines VII are reacted with hydrazine at reflux temperature in a lower alkanol or pyridine for a period of 5-24 hours to provide the corresponding 6-heteroaryl-3-hydrazinopyridazines VIII. Ring closure of the 3-hydrazino derivatives VIII with lower alkyl ($C_1$-$C_6$) orthoformates or formic acid provides compounds of formula X. Ring closure of the 3-hydrazino derivatives VIII with lower alkanoic ($C_2$-$C_4$) anhydrides, lower alkanoic ($C_2$-$C_4$) acid chlorides, orthoesters of lower alkanoic ($C_2$-$C_4$) acids, or diethoxymethyl alkanoates ($C_2$-$C_4$) provides compounds of formula IX wherein alkyl is $C_1$-$C_3$ carbon atoms. The ring closures may be carried out with or without catalysis by bases such as pyridine or tri(lower alkyl)amines. Ring closures with lower alkyl orthoformates and orthoesters of lower alkanoic acids are preferably carried out without catalysis and without solvent, although an inert solvent may be used. The ring closures are usually accomplished by heating with or without a solvent at 50° C. to 175° C.

The novel 8-heteroaryl-1,2,4-triazolo[4,3-b]pyridazines of the present invention are prepared in accordance with the following reaction scheme.

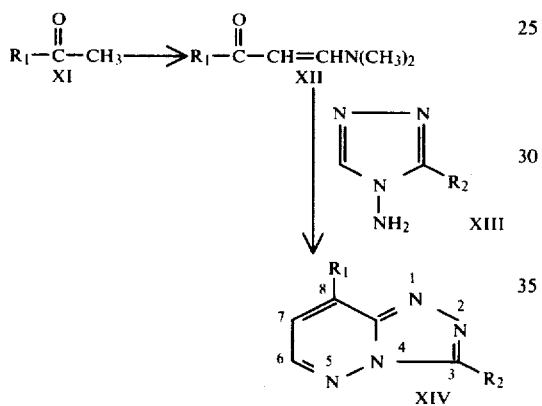

wherein $R_1$ and $R_2$ are as hereinbefore defined. In accordance with the above reaction scheme, an acetyl heterocycle such as 2- and 3-acetylpyridine, 2- and 3-acetylthiophene or 2- and 3-acetylfuran is reacted with N,N-dimethylformamide dimethyl acetal or N,N-dimethylformamide diethyl acetal to give derivatives of formula XII. Reaction of the 3-dimethylamino-1-(heteroaryl)-2-propen-1-ones XII with a 4-amino-1,2,4-triazole XIII gives the 8-heteroaryl-1,2,4-triazolo[4,3-b]pyridazines XIV. The reaction is carried out in refluxing xylene for 10-24 hours. Alternatively the reaction may be carried out by heating the reactants without solvent at 100°-150° C. for 10-24 hours. The novel compounds of this invention wherein $R_1$ is a 2-pyridyl-1-oxide or 3-pyridyl-1-oxide group may be prepared from the corresponding 2-pyridyl and 3-pyridyl derivatives by reaction with hydrogen peroxide or a peracid such as m-chloroperbenzoic acid. Other reagents suitable for introduction of the 1-oxide function into pyridine and pyridine derivatives may also be employed.

The novel compounds of the present invention possess central nervous system activity at non-toxic doses and as such are useful as anxiolytic agents. That is, they produce certain responses in standard tests with laboratory animals which are known to correlate well with relief of anxiety in man.

The anti-anxiety properties of the novel compounds of the present invention have been established in a test which indicates anxiolytic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of polysorbate 80 to groups of at least 4 rats. At 30 or 60 minutes, the rats were treated intravenously with pentylenetetrazole at a dose of 23 mg./kg. of body weight. This dose is estimated to cause clonic seizures in 99% of unprotected rats. The test compounds are considered active if they protect 50% or more of the rats from clonic seizures. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp. 237-288 (1971)] that there is a high degree of correlation between antagonism of pentylenetetrazole seizures in rats and anti-anxiety effects in higher warm-blooded animals. The following representative compounds of the present invention listed in Table I have been shown to possess anxiolytic activity when tested as described above.

TABLE I

Protection Against Clonic Seizures Caused by Pentylenetetrazole in Rats

| Compound | Result |
|---|---|
| 3-methyl-6-(3-pyridyl)-1,2,4-triazolo[4,3-b]pyridazine | Active |
| 3-methyl-6-(2-pyridyl)-1,2,4-triazolo[4,3-b]pyridazine | Active |
| 3-methyl-6-(2-thienyl)-1,2,4-triazolo[4,3-b]pyridazine | Active |
| 6-(2-thienyl)-1,2,4-triazolo[4,,3,b]-pyridazine | Active |
| 6-(3-pyridyl)-1,2,4-triazolo[4,3b]-pyridazine | Active |
| 8-(3-pyridyl)-1,2,4-triazolo[4,3-b]-pyridazine | Active |

BRAIN-SPECIFIC BENZODIAZEPINE RECEPTOR BINDING ASSAY

Another test utilized for the determination of anxiolytic activity is the measurement of the ability of test compounds to inhibit the binding of tritiated benzodiazepines to brain-specific receptors of warm-blooded animals. A modification of the method described by R. F. Squires et al. Nature, 266: No. 21, pg. 732, (1977) and H. Mohler et al. Science, 198: pg. 849, (1977) was employed.

Male albino rats (Wistar strain, weighing 150-200 g. each) were obtained from Royalhart Farms. $^3$H-methylflunitrazepam (84.3 Ci/mmol) was obtained from New England Nuclear. The test compounds were solubilized in dimethylformamide.

Whole cortex of rats was homogenized gently in 10 volumes of ice-cold 0.32 M. sucrose, centrifuged twice at 1000 g for 10 minutes and then recentrifuged at 30,000 g for 20 minutes to produce a crude $P_2$-synaptosomal fraction. The $P_2$-fraction was resuspended in 10 volumes of hypotonic 10 mM. Tris.HCl (pH 7.5) and frozen (−20° C.) until time of use. Frozen $P_2$ preparations were thawed and resuspended in eight times the original homogenizing volume at time of assay.

The binding assay consisted of 300 μl. of the $P_2$-fraction suspension (0.1-0.3 mg. protein), 100 μl. of test drug and 100 μl. of $^3$H-flunitrazepam (1.0 nM., final concentration) which was added to 1.5 ml. of 50 mM. Tris.HCl (pH 7.5). Non-specific binding controls and total binding controls received 100 μl. of clonazepam (1 μM. final concentration) and 100 μl. of buffer, respectively, in place of the test compound. Incubation for 30 minutes proceeded in ice and was terminated by filtration, under vacuum, through Whatman GF/C glass fiber filters. The filters were washed twice with 5 ml. of ice-cold 50 mM. Tris.HCl (pH 7.5) and placed in scintillation vials. 10 ml. of Beckman Ready-Solve HP was added and the radioactivity determined in a Beckman Scintillation Counter.

Compounds which exhibited the ability to inhibit ³H-benzodiazepine binding by 10% were considered to be active. Inhibition of binding was calculated by the difference between specific binding with no drug and specific binding in the presence of test compound, divided by the specific binding with no drug, X 100.

Representative compounds of the present invention which are active when tested by the ³H-benzodiazepine binding assay are listed in Table II.

TABLE II

| Inhibition of the Binding of ³H-Benzodiazepine Brain-specific Receptors of Rats | |
|---|---|
| Compound | Result |
| 3-methyl-6-(3-pyridyl)-1,2,4-triazolo-[4,3-b]pyridazine | Active |
| 3-methyl-6-(2-thienyl)-1,2,4-triazolo-[4,3-b]pyridazine | Active |
| 6-(2-thienyl)-1,2,4-triazolo[4,3-b]pyridazine | Active |
| 6-(3-pyridyl)-1,2,4-triazolo[4,3-b]pyridazine | Active |
| 3-methyl-6-(3-thienyl-1,2,4-triazolo-[4,3-b]pyridazine | Active |
| 6-(3-thienyl)-1,2,4-triazolo[4,3-b]pyridazine | Active |

Another test which has been used to assess anti-anxiety effects is a non-conditioned passive avoidance procedure described by J. R. Vogel, B. Beer and D. E. Clody, "A Simple and Reliable Conflict Procedure for Testing Anti-Anxiety Agents", Psychopharmacologia, 21, 1–7 (1971). A conflict situation is induced in rats by a modification of this method.

Groups of 6 naive, Wistar strain rats, weighing 200–240 g. each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 or 60 minutes each rat was placed in an individual black plexiglass chamber. A 10% dextrose solution was available ad libitum from a tap located in the rear of the chamber. A 0.3 milliampere DC shocking current was established between the stainless steel grid floor and the tap. After 20 seconds of non-shocked drinking, an alternating 5 second "shock-on" and 5 second "shock-off" cycle began and continued for a total of 5 minutes. The number of shocks taken by each rat during the 5 minute interval was recorded and compared to a control group. The test compounds are considered active if the number of shocks received by the test group is significantly higher than the control group by the Mann-Witney U test.

The novel compounds of the present invention have been found to be highly useful for meliorating anxiety in mammals when administered in amounts ranging from about 0.1 mg. to about 35.0 mg./kg. of body weight per day. A preferred dosage regimen for optimum results would be from about 0.5 mg. to about 5.0 mg./kg. of body weight per day. Such dosage units are employed that a total of from about 35 mg. to about 1.0 g. of active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have molecular weights of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg./ml. of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg./ml. of active ingredient are satisfactory.

The active compounds of the present invention may be orally administered, for example, with an inert diluent or with an assimilable edible carrier, or they may be enclosed in hard or soft shell capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

SPECIFIC DISCLOSURE

The following specific examples illustrate the preparation of the compounds of thepresent invention.

EXAMPLE 1

3-Methyl-6-(3-pyridyl)-1,2,4-triazolo[4,3-b]pyridazine

To a stirred solution of 13.0 g. of α-3-pyridyl-4-morpholine acetonitrile [J. O. C.: 37, 4465 (1972)] in 130 ml. of tetrahydrofuran under argon is added 75 drops of 30% potassium hydroxide in ethanol followed by a solution of 8.65 ml. of ethyl acrylate in 30 ml. of tetrahydrofuran added dropwise over a period of 30 minutes at a temperature of 22°-30° C. The resulting mixture is stirred at room temperature for 2 hours and evaporated to dryness in vacuo. The residue is extracted with two 50 ml. portions of ethyl ether. The extracts are filtered and the filtrate is evaporated to give 18.5 g. of γ-cyano-γ-3-pyridyl-4-morpholinebutyric acid ethyl ester as a clear gum.

To a solution of 18.5 g. of the preceding product in 90 ml. of glacial acetic acid is added 10 ml. of water. The reaction mixture is stirred and heated at reflux temperature for one hour, then is evaporated to dryness in vacuo. The evaporation step is repeated several times with toluene. The residue is partitioned between 30 ml. of water and methylene chloride. The organic phase is separated and the aqueous phase is extracted again with methylene chloride. The organic extracts are combined, treated with activated charcoal, dried with magnesium sulfate and evaporated in vacuo to give12.8 g. of an amber oil. To the oil is added 60 ml. of alcoholic hydrogen chloride which results in the immediate crystallization of a solid. The mixture is evaporated to dryness in vacuo. The residue is triturated with 30 ml. of cold acetone and the product is collected by filtration under a drying tube, washing with 20 ml. of cold acetone then with petroleum ether to give 11.3 g. of γ-oxo-3-pyridinebutyric acid ethyl ester hydrochloride as white crystals, m.p. 162°-164° C.

To a partial solution of 7.76 g. of the above ester hydrochloride in 75 ml. of ethanol is added 3.9 ml. of 99% hydrazine hydrate. The mixture is stirred and heated at the reflux temperature for 18 hours, then is evaporated to dryness in vacuo.

The residue is triturated with 30 ml. of water to obtain 3.45 g. of 5,6-dihydro-6-(3-pyridyl)-3(2H)-pyridazinone as a yellow solid, m.p. 175°-177° C.

A mixture of 14.0 g. of the preceding compound (prepared as described above), 20.0 g. of sodium m-nitrobenzenesulfonate and 14.08 g. of sodium hydroxide in 200 ml. of water is heated at reflux for 2 hours. The hot reaction mixture is treated with activated charcoal and filtered. The hot filtrate is adjusted to pH 7 by the addition of 21.64 g. of glacial acetic acid. The filtrate is cooled in ice to precipitate a solid which is collected by filtration to give 10.3 g. of a cream colored solid. This solid is essentially redissolved in ethanol then is filtered. The filtrate is cooled and filtered twice, to afford 4.1 g. of 6-(3-pyridyl)-3(2H)-pyridazinone as cream colored crystals, m.p. 200°-203° C.

The above product (4.1 g.) in 50 ml. of phosphorus oxychloride is warmed on a steam bath for 2 hours. The reaction mixture is filtered and the filtrate is evaporated in vacuo. The residue is cooled in ice and diluted with ice water. The pH of the mixture is adjusted to neutral with sodium hydroxide solution. The mixture is cooled in ice and filtered. The filter cake is sucked dry on a funnel, dissolved in methanol, dried over anhydrous sodium sulfate and evaporated in vacuo. The residue is washed with hexane to afford 3.5 g. of 3-chloro-6-(3-pyridyl)pyridazine as tan crystals, m.p. 154°-156° C.

A mixture of 0.5 g. of the preceding compound and 0.44 g. of acethydrazide (74%) in 25 ml. of n-butyl alcohol is heated at reflux temperature for 36 hours. The reaction mixture is concentrated free of volatiles and the residue is partitioned between methylene chloride and 1 N sodium hydroxide. The organic layer is dried over anhydrous sodium sulfate and filtered. The product is crystallized from the filtrate by the addition of hexane and the product is collected by filtration. The crystallization procedure is repeated on the filtrate to yield a total of 0.68 g. of the product of the Example as a light tan solid, m.p. 224°-225° C.

EXAMPLE 2

6-(3-Pyridyl)-1,2,4-triazolo[4,3-b]pyridazine

A mixture of 1.5 g. of 3-chloro-6-(3-pyridyl)pyridazine and 0.96 g. of formic acid hydrazide in 50 ml. of n-butyl alcohol is refluxed for 48 hours. The reaction mixture is concentrated, partitioned and crystallized as described in Example 1 to afford 1.0 g. of the product of the Example as a cream colored solid, m.p. 199°-200°.

EXAMPLE 3

3-Methyl-6-(2-pyridyl)-1,2,4-triazolo[4,3-b]pyridazine

To a stirred solution of 124 g. of the salt of morpholine and p-toluenesulfonic acid in 455 ml. of morpholine is added 50.0 g. of 2-pyridinecarboxaldehyde. The mixture is stirred and heated at 80° C. for one hour, then a partial solution of 32.6 g. of potassium cyanide in 22 ml. of water is added and the mixture is stirred for one hour at 100°-105° C. The mixture is cooled, poured into 2,200 ml. of 10% aqueous potassium carbonate solution and extracted several times with chloroform. The combined extract is washed with 1,500 ml. of 10% aqueous sodium bisulfite, dried with magnesium sulfate and evaporated in vacuo to give a solid. The solid is ground in a mortar and washed with petroleum ether on a filter until the filtrate is clear to obtain 83.6 g. of a tan solid.

A 62.5 g. amount of the above solid is dissolved in one liter of benzene, treated with activated charcoal and filtered. To the filtrate is added 2 liters of hexane. The mixture is chilled, then filtered to obtain 52.4 g. of α-(2-pyridyl)-4-morpholineacetonitrile as tan crystals, m.p. 99°–100° C.

To a solution of 40.5 g. of the preceding compound in 500 ml. of tetrahydrofuran under argon is added 240 drops of 30% potassium hydroxide in ethanol followed by a solution of 27 ml. (25 g.) of ethyl acrylate in 200 ml. of tetrahydrofuran added dropwise over a period of 20 minutes at a temperature of 22°–30° C. The mixture is stirred at room temperature for 2 hours, then is evaporated to dryness in vacuo. The evaporation step is repeated with toluene. The residue is extracted with 250 ml. of ethyl ether. The extracts are filtered and the ether filtrate is evaporated to dryness and the residue triturated with petroleum ether. The solid is filtered and ground in a mortar to give 54.5 g. of γ-cyano-γ-2-pyridyl-4-morpholinebutyric acid ethyl ester as white crystals, m.p. 79°–81° C.

A solution 21.2 g. of the above compound in 95 ml. of glacial acetic acid and 10.5 ml. of water is stirred and heated at the reflux temperature for one hour. The mixture is evaporated to dryness in vacuo and the evaporation procedure is repeated with three 100 ml. portions of toluene. The resulting residue is partitioned between 50 ml. of water and methylene chloride. The organic layer is separated and the aqueous solution is extracted again with methylene chloride. The organic layer is separated, combined with the previous extract, treated with activated charcoal, dried with magnesium sulfate and filtered. The filtrate is evaporated in vacuo to give 14.9 g. of an amber oil. To the oil is added 70 ml. of alcoholic hydrogen chloride. The mixture is evaporated to dryness in vacuo giving a yellow solid. The solid is triturated with 30 ml. of cold acetone and is filtered, washed with 20 ml. of cold acetone followed by petroleum ether to give 11.7 g. of an off-white solid. The solid is recrystallized from 200 ml. of acetone to give 10.1 g. of γ-oxo-2-pyridinebutyric acid ethyl ester hydrochloride as pink crystals, m.p. 128°–130° C.

To a solution of 4.5 g. of the preceding product in 45 ml. of ethanol is added 2.7 ml. of 99% hydrazine hydrate. The mixture is stirred and heated at the reflux temperature for 18 hours then, is evaporated to dryness in vacuo giving an orange solid. The solid is triturated with 20 ml. of water to provide 2.53 g. of 5,6-dihydro-6-(2-pyridyl)-3(2H)-pyridazinone as a yellow solid, m.p. 179°–184° C.

A mixture of 14.0 g. of the preceding compound (prepared as described above), 20.0 g. of sodium m-nitrobenzenesulfonate and 14.08 g. of sodium hydroxide in 200 ml. of water is heated at reflux for 2 hours. The reaction mixture is treated with activated charcoal and filtered. The filtrate is rendered neutral by the addition of 21.64 g. of glacial acetic acid and the mixture is cooled in ice and filtered to afford 6.9 g. of 6-(2-pyridyl)-3(2H)-pyridazinone as a cream colored solid, m.p. 240°–243° C.

The above compound (6.9 g.) and 40 ml. of phosphorus oxychloride is heated at reflux for 3 hours. The volatiles are removed in vacuo and the concentrate is stirred with ice and water. The reaction mixture is rendered neutral with 10 N sodium hydroxide and the resulting solid is collected by vacuum filtration and washed with water. The solid is dissolved in 300 ml. of methanol, dried over anhydrous sodium sulfate, treated with activated charcoal and filtered. The filtrate is concentrated to a small volume and cooled in ice to afford 4.7 g. of 3-chloro-6-(2-pyridyl)pyridazine as cream colored crystals, m.p. 125°–126° C.

A mixture of 2.0 g. of the preceding compound and 1.5 g. of acethydrazide (74%) in 50 ml. of n-butyl alcohol is refluxed for 18 hours. The reaction mixture is concentrated free of volatiles and the concentrate is partitioned between dilute aqueous sodium hydroxide and methylene chloride. The organic layer is dried over anhydrous sodium sulfate and evaporated in vacuo to give a solid. The solid is crystallized from methylene chloride-hexane to give 1.9 g. of the product of the Example as light tan crystals m.p. 183°–185° C.

EXAMPLE 4

6-(2-Pyridyl)-1,2,4-triazolo[4,3-b]pyridazine

A mixture of 1.0 g. of 3-chloro-6-(2-pyridyl)pyridazine and 0.6 g. of formic acid hydrazide in 50 ml. of n-butyl alcohol is heated at the reflux temperature for 18 hours. The volatiles are removed in vacuo and the residue is partitioned between dilute aqueous sodium hydroxide and methylene chloride. The organic layer is dried over sodium sulfate and filtered. The filtrate is evaporated and the residue is crystallized from methylene chloride-hexane to afford 1.0 g. of the desired product as off-white to yellow crystals, m.p. 191°–192° C.

EXAMPLE 5

3-Methyl-6-(2-thienyl)-1,2,4-triazolo[4,3-b]pyridazine

A mixture of 14.4 g. of 4,5-dihydro-6-(2-thienyl)-3(2H)-pyridazinone, 20.0 g. of sodium m-nitrobenzene sulfate and 14.08 g. of sodium hydroxide in 200 ml. of water is refluxed for 2 hours. The reaction mixture is treated with activated charcoal while hot, then is filtered. The warm filtrate is adjusted to pH 7 by the addition of 15.6 g. of glacial acetic acid and is cooled in ice. The resulting solid is collected by filtration, washed with water and air dried to afford 7.5 g. of 6-(2-thienyl)-3(2H)-pyridazinone as a cream colored solid m.p. 180°–182° C.

A 3.5 g. amount of the preceding compound and 40 ml. of phosphorus oxychloride is heated on a steam bath for 30 minutes to provide complete solution. The volatiles are removed in vacuo and the concentrate is scratched with crushed ice and cold water to provide a tan solid which is collected by filtration, washed with water and air dried. The solid is dissolved in methylene chloride-hexane, treated with activated charcoal, filtered and recrystallized to give 3.5 g. of 3-chloro-6-(2-thienyl)pyridazine as a cream colored solid, m.p. 160°–163° C.

A mixture of 1.5 g. of the above product and 1.19 g. of acethydrazide (74%) in 50 ml. of n-butyl alcohol is heated at the reflux temperature for 48 hours. The volatiles are removed in vacuo and the residue is dissolved in methylene chloride and washed with dilute aqueous sodium hydroxide.

The organic layer is dried over anhydrous sodium sulfate and filtered. The filtrate is evaporated in vacuo and the residue is recrystallized from methylene chloride-hexane to afford 1.1 g. of the desired product as a cream colored solid, m.p. 152°–153° C.

EXAMPLE 6

6-(2-Thienyl)-1,2,4-triazolo[4,3-b]pyridazine

A mixture of 1.0 g. of 3-chloro-6-(2-thienyl)pyridazine and 0.6 g. of formic acid hydrazide in 50 ml. of n-butyl alcohol is heated at the reflux temperature for 18 hours. The volatiles are removed and the residue is partitioned between dilute aqueous sodium hydroxide and methylene chloride. The organic layer is dried over anhydrous sodium sulfate, filtered and evaporated. The residue is recrystallized from methylene chloride:hexane to afford a tan solid. The solid is recrystallized from acetone:hexane to give 0.5 g. of the desired product as cream colored crystals, m.p. 155°–159° C.

EXAMPLE 7

3-Methyl-6-(3-thienyl)-1,2,4-triazolo[4,3-b]pyridazine

A 190.22 g. amount of p-toluenesulfonic acid is partially dissolved in 500 ml. of tetrahydrofuran with stirring then 174.2 g. of morpholine is added in small portions with cooling over a 30 minute period. Finally 99.0 g. of 3-thiophenecarboxaldehyde is added in small portions and the reaction mixture is refluxed for 18 hours.

The reaction mixture is cooled to room temperature and a solution of 61.9 g. of potassium cyanide in 100 ml. of water is added. The mixture is stirred and refluxed for 18 hours. The reaction mixture is concentrated free of volatiles and the residue is partitioned between water and methylene chloride. The organic layer is washed with aqueous sodium bisulfite, dried over anhydrous sodium sulfate, passed through a short column of hydrated magnesium silicate and evaporated in vacuo. The residue is recrystallized from methylene chloride-hexane to afford 137.42 g. of γ-3-thienyl-4-morpholineacetonitrile as cream colored crystals.

A 50.5 g. amount of the preceding compound is dissolved in 500 ml. of tetrahydrofuran at room temperature and then 20 ml. of 30% potassium hydroxide in ethanol is added followed by the rapid addition of 50 ml. of ethyl acrylate. After stirring for 3 hours an additional 20 ml. of 30% potassium hydroxide in ethanol and 50 ml. of ethyl acrylate is added. The reaction mixture is allowed to stir for 48 hours at room temperature in a stoppered flask. The reaction is concentrated free of volatiles. The residue is dissolved in methylene chloride and passed through a column of hydrous magnesium silicate. The filtrate is concentrated to provide 88 g. of γ-cyano-γ-3-thienyl-4-morpholinebutyric acid ethyl ester as a yellow oil.

A mixture of 68.0 g. of the preceding product in 200 ml. of glacial acetic acid and 40 ml. of water is heated on a steam bath for 2 hours. To the mixture is added 13 ml. of hydrazine hydrate and the reaction mixture is heated on a steam bath for 16 hours. The mixture is concentrated free of volatiles in vacuo and 400 ml. of cold water is added to the residue. Scratching and cooling in ice affords a cream colored solid which is collected by filtration and air dried. The solid is recrystallized from methylene chloride-hexane to give 8.0 g. of 4,5-dihydro-6-(3-thienyl)-3(2H)-pyridazinone as a cream colored solid, m.p. 163°–165° C.

A mixture of 14.4 g. of the above produce (prepared as described), 20.0 g. of sodium m-nitrobenzene sulfate and 14.08 g. of sodium hydroxide in 200 ml. of water in a reaction flask is placed in a preheated mantel and heated at the reflux temperature for one hour. The reaction mixture is treated with activated charcoal while hot and is filtered. The filtrate is rendered neutral by the addition of 20 g. of glacial acetic acid. The resulting solid is cooled in ice, filtered, washed with water and dried to afford an off-white solid. The solid is recrystallized from acetone-hexane to give 5.9 g of 6-(3-thienyl)-3-(2H)-pyridazinone as an off-white solid, m.p. 181°–183° C.

The above product (5.9 g.) in 75 ml. of phosphorus oxychloride is heated on a steam bath for 45 minutes. The volatiles are removed in vacuo and the oily concentrate is stirred with ice and water. The precipitated product is collected by filtration, washed with water and air dried to give a tan solid. The solid is recrystallized from methylene chloride-hexane to provide 5.0 g. of 3-chloro-6-(3-thienyl)-pyridazine as a tan solid, m.p. 169°–171° C.

A mixture of 1.5 g. of the preceding compound and 1.1 g. of acethydrazide (74%) in 50 ml. of n-butyl alcohol is heated at the reflux temperature for 18 hours. The reaction mixture is concentrated to a yellow gummy solid which is partitioned between methylene chloride and 1 N sodium hydroxide. The organic layer is dried over anhydrous sodium sulfate, filtered and evaporated. The residue is recrystallized from methylene chloride-hexane to give a gray solid. The solid is recrystallized from acetone-methylene chloride-hexane to give 1.0 g. of the desired product as cream colored crystals, m.p. 154°–156° C.

EXAMPLE 8

6-(3-Thienyl)-1,2,4-triazolo[4,3-b]pyridazine

A mixture of 1.5 g. of 3-chloro-6-(3-thienyl)pyridazine and 0.96 g. of formic acid hydrazide in 50 ml. of n-butyl alcohol is heated at the reflux temperature for 48 hours. The reaction mixture is concentrated free of volatiles and the residue is partitioned between dilute sodium hydroxide and methylene chloride. The organic layer is dried over anhydrous sodium sulfate, filtered and evaporated. The residue is recrystallized from methylene chloride-hexane to give a solid. The solid is recrystallized from acetone-hexane to provide 1.0 g. of the product of the Example as a orange-cream solid, m.p. 189°–192° C.

EXAMPLE 9

3-Methyl-6-(3-pyridyl)-1,2,4-triazolo[4,3-b]pyridazine, pyridine-1-oxide

A mixture of 2.0 g. of 3-methyl-6-(3-pyridyl)-1,2,4-triazolo [4,3-b]pyridazine, 25 ml. of glacial acetic acid and 2 ml. of 30% hydrogen peroxide is heated on a steam bath for 2 hours. The solvent is removed to give the product of the Example.

EXAMPLE 10

6-(3-Pyridyl)-1,2,4-triazolo[4,3-b]pyridazine, pyridine-1-oxide

A mixture of 1.0 g. of 6-(3-pyridyl)-1,2,4-triazolo[4,3-b]pyridazine, 20 ml. of glacial acetic acid and 5 ml. of 30% hydrogen peroxide is heated on a steam bath for 4 hours. The solvent is removed to give the product of the Example.

EXAMPLE 11

3-Methyl-6-(2-pyridyl)-1,2,4-triazolo[4,3-b]pyridazine, pyridine-1-oxide

A mixture of 4.0 g. of 3-methyl-6(2-pyridyl)-1,2,4-triazolo [4,3-b]pyridazine, 50 ml. of glacial acetic acid and 5 ml. of 30% hydrogen peroxide is heated on a steam bath for 4 hours. The solvent is removed to give the product of the Example.

EXAMPLE 12

6-(2-Pyridyl)-1,2,4-triazolo[4,3-b]pyridazine, pyridine-1-oxide

A mixture of 3.0 g. of 6-(2-pyridyl)-1,2,4-triazolo-[4,3-b]pyridazine, 30 ml. of glacial acetic acid and 5 ml. of 30% hydrogen peroxide is heated on a steam bath for 3 hours. The solvent is removed to give the product of the Example.

EXAMPLE 13

3-Methyl-6-(2-furyl)-1,2,4-triazolo[4,3-b]pyridazine

As for Example 5, 4,5-dihydro-6-(2-furyl)-3(2H)-pyridazinone is converted to 3-chloro-6-(2-furyl)pyridazine. A 1.5 g. sample of the preceding compound, 1.2 g. of acethydrazide in 50 ml. of n-butyl alcohol is refluxed for 48 hours. The solvent is removed under reduced pressure and the residue is partitioned between dichloromethane and dilute sodium hydroxide. The dichloromethane layer is washed with water, dried over magnesium sulfate, filtered and concentrated. The residue is purified by conventional means to give the product of the Example.

EXAMPLE 14

3-Ethyl-6-(3-pyridyl)-1,2,4-triazolo[4,3-b]pyridazine

As for Example 2, a mixture of 3-chloro-6-(3-pyridyl)pyridazine (2.0 g.) and propionic acid hydrazide in 60 ml. of n-butyl alcohol is refluxed for 48 hours to give the product of the Example.

EXAMPLE 15

3-Ethyl-6-(2-pyridyl)-1,2,4-triazolo[4,3-b]pyridazine

As for Example 4, a mixture of 1.0 g. of 3-chloro-6-(2-pyridyl)pyridazine, propionic acid hydrazide and 50 ml. of n-butyl alcohol is refluxed for 48 hours to give the product of the Example.

EXAMPLE 16

8-(3-Pyridyl)-1,2,4-triazolo[4,3-b]pyridazine

A mixture of 50.0 g. of 3-acetylpyridine and 60 ml. of N,N-dimethylformamide dimethylacetal is refluxed for 16 hours. The solvent is removed in vacuo and hexane is added. The crystalline solid is separated and recrystallized from dichloromethane-hexane to give 36.5 g. of 3-dimethylamino-1-(3-pyridyl)-2-propen-1-one, m.p. 66°–67° C.

The preceding compound is reacted with 4-amino-1,2,4-triazole in refluxing xylene for 16 hours to give the product of Example as crystals, m.p. 195°–196° C.

EXAMPLE 17

8-(3-Thienyl)-1,2,4-triazolo[4,3-b]pyridazine

As for Example 16, a mixture of 3-dimethylamino-1-(3-thienyl)-2-propen-1-one, 4-amino-1,2,4-triazole and xylene is refluxed for 16 hours to give the product of the Example.

EXAMPLE 18

8-(2-Pyridyl)-1,2,4-triazolo[4,3-b]pyridazine

As for Example 16, a mixture of 3-dimethylamino-1-(2-pyridyl)-2-propen-1-one, 4-amino-1,2,4-triazole and xylene is refluxed for 16 hours to give the product of the Example.

EXAMPLE 19

8-(2-Furyl)-1,2,4-triazolo[4,3-b]pyridazine

As for Example 16, a mixture of 3-dimethylamino-1-(2-furyl)-2-propen-1-one, 4-amino-1,2,4-triazole and xylene is refluxed for 16 hours to give the product of the Example.

We claim:

1. A compound selected from the group consisting of those of the formula:

wherein $R_1$ is selected from the group consisting of:

where R' is hydrogen or lower alkyl $(C_1-C_3)$; and $R_2$ is hydrogen or lower alkyl $(C_1-C_3)$.

2. The compound according to claim 1, 3-methyl-6-(3-pyridyl)-1,2,4-triazolo[4,3-b]pyridazine.

3. The compound according to claim 1, 6-(3-pyridyl)-1,2,4-triazolo[4,3-b]pyridazine.

4. The compound according to claim 1, 3-methyl-6-(2-pyridyl)-1,2,4-triazolo[4,3-b]pyridazine.

5. The compound according to claim 1, 6-(2-pyridyl)-1,2,4-triazolo[4,3-b]pyridazine.

6. The compound according to claim 1, 3-methyl-6-(2-thienyl)-1,2,4-triazolo[4,3-b]pyridazine.

7. The compound according to claim 1, 6-(2-thienyl)-1,2,4-triazolo[4,3-b]pyridazine.

8. The compound according to claim 1, 3-methyl-6-(3-thienyl)-1,2,4-triazolo[4,3-b]pyridazine.

9. The compound according to claim 1, 6-(3-thienyl)-1,2,4-triazolo[4,3-b]pyridazine.

10. The compound according to claim 1, 8-(3-pyridyl)-1,2,4-triazolo[4,3-b]pyridazine.

11. The compound according to claim 1, wherein $R_1$ consists of

12. The compound according to claim 1, wherein $R_1$ consists of
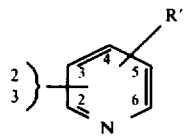
13. The compound according to claim 1, wherein $R_1$ consists of
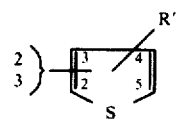
14. The compound according to claim 1, 8-(2-furyl)-1,2,4-trazolo[4,3-b]pyridazine.
* * * * *